United States Patent [19]

Chen et al.

[11] 4,064,534
[45] Dec. 20, 1977

[54] SYSTEM FOR MONITORING THE PRODUCTION OF ITEMS WHICH ARE INITIALLY DIFFICULT TO PHYSICALLY INSPECT

[75] Inventors: Tung Chang Chen, Villanova; Thomas M. Chen, Doylestown, both of Pa.

[73] Assignee: Leone International Sales Corporation, Bridgeton, N.J.

[21] Appl. No.: 678,467

[22] Filed: Apr. 20, 1976

[51] Int. Cl.² ................................................. H04N 7/18
[52] U.S. Cl. ..................................... 358/107; 358/100; 358/101; 358/106; 250/560; 250/565
[58] Field of Search ............... 358/100, 101, 106, 107; 178/DIG. 36; 235/151.3; 250/560, 565

[56] References Cited

U.S. PATENT DOCUMENTS

| | | | |
|---|---|---|---|
| 2,798,605 | 7/1957 | Richards | 358/106 |
| 3,216,311 | 11/1965 | Bibbero et al. | 178/DIG. 36 |
| 3,740,467 | 6/1973 | Kubo | 178/6.8 |

Primary Examiner—Robert L. Griffin
Assistant Examiner—Edward L. Coles
Attorney, Agent, or Firm—William E. Cleaver

[57] ABSTRACT

The present system provides a means to record an image of an item which is extremely difficult to inspect because of its peculiar shape or because the person who is inspecting it cannot come in close proximity thereto, such as red hot glass being measured for form and size immediately upon being formed into a bottle. The present system employs a television camera and logic circuitry to electronically compare the profile of said image against a standard item whereby the item being inspected or measured can either be rejected or accepted.

10 Claims, 12 Drawing Figures

SYSTEM FOR MONITORING THE PRODUCTION OF ITEMS WHICH ARE INITIALLY DIFFICULT TO PHYSICALLY INSPECT

BACKGROUND

In the mass production of items which are initially formed in a hot state or a molten state, it has been the practice to effect a quality control when such items have cooled off and/or have been produced to at least their rough cool state. The unfortunate aspect of said production technique is that when an item which is being made by such a production scheme is found to be unacceptable, because of a fault in the production technique, a great deal of scrap has been produced. In other words, by the time that a cooled item is measured in such a procedure, it has been followed by many other items on the production line which have been made in a similar way. If any cooled item in the production line has incorrect dimensions, then there is a strong likelihood that the following items on the production line have the same wrong dimensions.

The present system provides a means to measure a production item in its "hot" state; and, if its dimensions are unacceptable, the person running the production line will be alerted and can either correct the problem while production continues, or shut down the system and correct the fabrication difficulty.

SUMMARY

The present invention is described in connection with a bottle fabrication means. Initially an acceptable bottle (a standard bottle) is loaded on a conveyor belt and passed through a reading station. In the reading station, at some instant in time, the standard bottle is located between a screen member and a television (TV) camera. The screen member is illuminated from the side opposite the bottle so that the bottle appears as an opaque item to the TV camera and the opaque image is "recorded" by said camera. The video signals produced by the TV camera are converted into digital form by the present system and accordingly a number of measurements of the bottle are recorded in digital signal form and located into a memory device. For instance the flatness of the top of the bottle, the width of the threads at the top of the bottle, the contour of the bottle and the location at which the binding ring (for twist-off caps) is crimped are typical parameters which are electronically recorded or measured with respect to the standard bottle and are stored in the memory. Thereafter "red hot" bottles, as they come from the molding machine, are loaded onto the conveyor belt and passed through the same reading station. Measurements of the same parameters of the "red hot" bottles are compared against the standard measurements; and, if the measurements of the "red hot" bottle differ, beyond certain tolerances, the present system alerts the person operating the system or can automatically shut down production.

The features and objects of the present invention will be better understood from the following description taken in connection with the drawings wherein.

Figure 1:
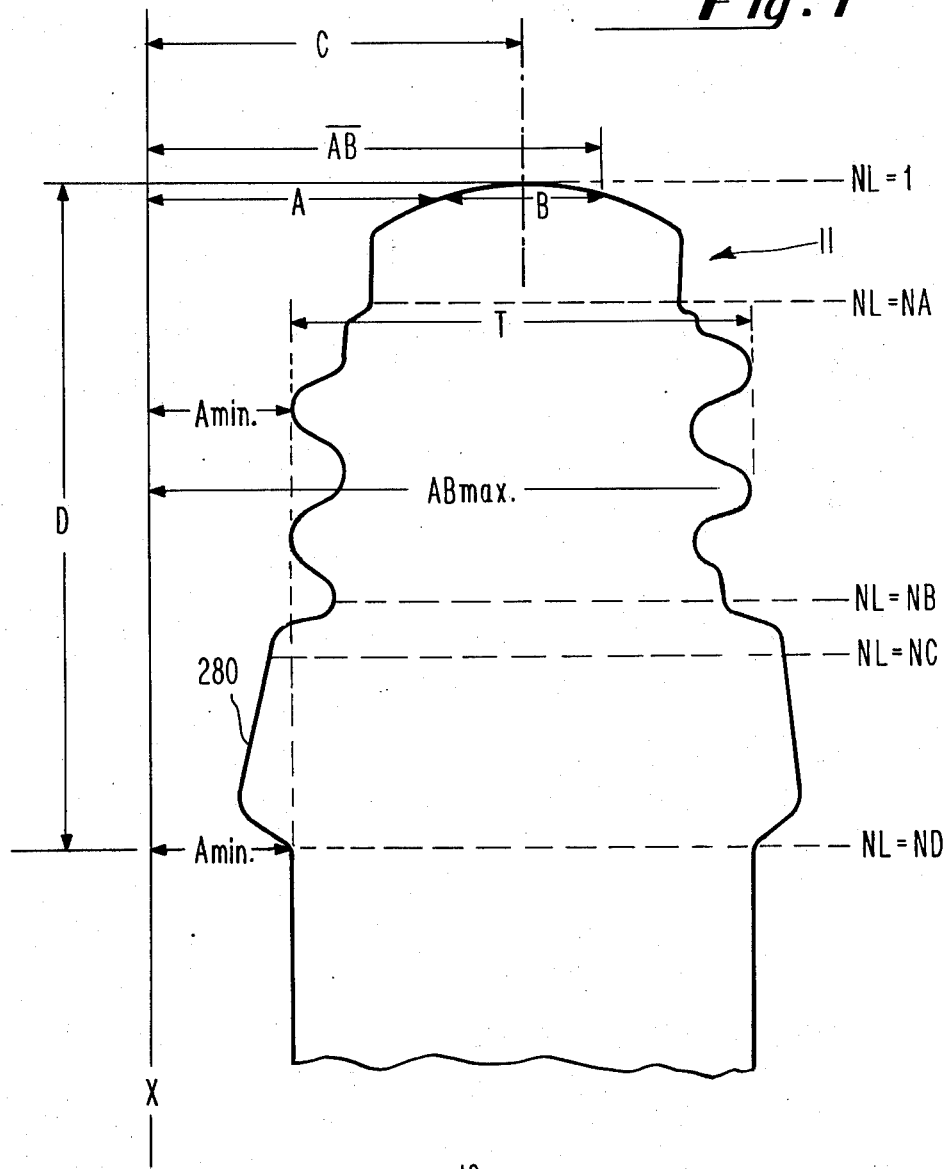
FIG. 1 is a contour of a bottle showing certain parameter dimensions thereon.

Consider FIG. 1, which is the contour of a bottle which is threaded at the top and which will use what is commonly called a twist-off cap. The manufacturer of such a bottle is concerned about a number of things. In the first instance, the bottle should have a flat top for purposes of sealing, and further for purposes of being assured that the user of the bottle does note in some way cut himself. Secondly, the fabricator of the bottle is concerned that the threads on the bottle are formed to a particular contour and/or set of dimensions, so that the twist-off caps, which he buys from a vendor or which he manufactures himself, can in fact be properly and automatically threaded onto the bottle. In the third instance, the fabricator of the bottle wants to be certain that the point on the bottle, whereat the binder ring is crimped onto the twist-off cap is at the proper location because the machine which automatically caps the bottle will always be attempting to crimp the binder ring at the same position. Finally, and probably most importantly, the fabricator of the bottle would like to be able to learn at any early time in the production whether or not the bottles that he is manufacturing compare favorably with a bottle that he has already manufactured and which is an acceptable bottle. He would like to learn of this discrepancy as soon as the bottle comes out of the molding machine so that in the event that his production line in commencing to produce bottles which are unacceptable, he can correct the fabrication difficulty before he has produced a large number of bottles which will have to be discarded; i.e., which will be considered scrap.

Figure 1A:
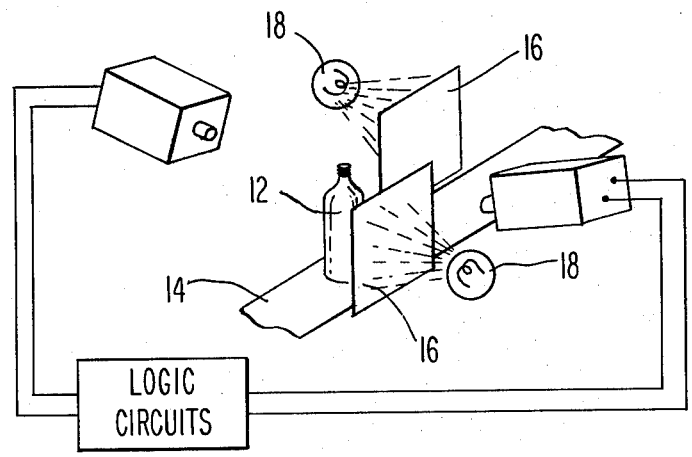
FIG. 1A depicts a reading station.

FIG. 1A depicts a reading station with two TV cameras located above a bottle and facing 180° from one another. The bottle 12 is located on a conveyor belt 14. As the bottle travels along the conveyor belt 14, it is seen by a first TV camera as an image against a screen 16 which is lighted by a source 18 and thereafter by a second TV camera, from another side, and as imaged in front of a second screen.

Bearing the above concerns in mind, if we examine FIG. 1, we find that certain masurements can be made; and if those measurements are compared against a standard bottle, the concerns of the manufacturer will be alleviated in great measure. With respect to the flatness of the top of the bottle, it has been determined that if the top of the bottle is viewed from an angle looking down at the bottle, then the top of the bottle will appear to have an arcuate shaped dimension; and if indeed it is flat, the arc will be symmetrical. Another reason for viewing the top of the bottle from an angle is that one half of the bottle will not prevent the camera from seeing the other half of the bottle. It has been found that there is an advantage if more than one camera is used. For instance, when two cameras are employed, each sees 180° from a position looking down on the bottle and from opposite sides of the bottle. The cameras are connected to have their signals dealt with separately and alternatively. Accordingly, the present system effects what is called a symmetry test which will be described in more detail hereinafter. If we examine FIG. 1 which shows a symmetrical arcuate bottle top, we note that the distance from line X to the center is the dimension C. Now if the bottle is symmetrical, then $C - A = A + B - C$, and if we rearrange the terms, we have $2C = A + B + A = \overline{AB} + A$ and since $2C =$ constant, then $\overline{AB} + A$ equals a constant. Therefore, if we can determine $\overline{AB} + A$ is a constant, we can determine that the bottle is symmetrical.

As just mentioned, if the foregoing equations are considered for the moment it becomes apparent that if the curvature being examined, such as line 13, is symmetrical then the distance $\overline{AB} + A$ will remain constant. As will be better understood hereinafter, the present system scans the profile of the bottle and measures the distance $\overline{AB} + A$ repeatedly as the scan continues downward in a vertical direction. The system operates to compare one measurement of $\overline{AB} + A$ with the succeeding measurement of that same distance and as long as the values remain equal or constant, then the bottle is considered to be symmetrical. This test will also indicate whether or not the bottle is leaning (possibility of a curved base), which would indicate an infirmity.

Further, as can be seen in FIG. 1, the width of the thread (T) is to be measured and this can be measured by determining "A min" and "$\overline{AB}$ max." When these two values have been determined, then "A min" can be subtracted from "$\overline{AB}$ max" and the width of the thread "T" will have been determined. As indicated earlier, the width of the thread is measured against, or compared against, a standard bottle, and if the thread width is within some tolerance of the value of the standard bottle, then the bottle being fabricated is considered acceptable insofar as that parameter is concerned. The present system works to scan the image of the bottle, making a determination in digital signal form of what "A min" is, as well as a determination in digital signal form of what "AB max" is. Thereafter these values are subtracted one from the other and the value of T is determined.

Further as can be seen in FIG. 1, the distance D is determined by determining when the bottle has an A value equal to or greater than the first "A min" value which was determined in connection with the determination of the thread width but which second "A min" value is further down the bottle than the point NC. As was described above, this last determination is meaningful because the bottle fabricator wants to know that the distance D is the proper distance within certain tolerances so that the binder ring can be crimped onto the twist-off cap when the twist-off cap is fitted over the top of the bottle.

Finally the maker of the bottles wants to know that the bottle is following the contour of the standard bottle so that there are no distortions. The manufacturer effects a check on the contour of the bottle by doing a line by line check, the details of which will be better understood as the circuitry is described hereinafter.

It should be understood that at the reading station in the preferred embodiment, there are three screens and three associated TV cameras. The TV cameras are located 120° apart and the screens are located 120° apart so that the bottle in the reading station is seen from three different positions. However, in this discussion we will only deal with one TV camera since all three TV cameras operate in exactly the same way. It should also be understood that there need not be three camera positions; there could be more or less.

It should be further understood that the TV camera which is employed in this system is a standard TV camera such as a Model 1981 manufactured by Impossible Electronics, Inc., and the output signals from the standard TV camera include a video signal plus the normal horizontal sync signals, the equalizing signals and the vertical sync signals. It should also be understood that the camera scans 30 frames per second of odd lines and 30 frames per second of even lines in the standard way. A number of signals are generated initially in response to the signals coming from the TV camera. The following table of the signals generated and what they mean will be helpful in this description:

| Letter Designation | Meaning |
| --- | --- |
| HSLP | Horizontal sync leading edge pulse |
| HSTP | Horizontal sync trailing edge pulse |
| OVSP | Odd vertical sync pulse |
| EVSP | Even vertical sync pulse |
| VSP | Vertical sync pulse |
| BN | Video signal |
| BNLP | Video signal leading edge pulse |
| BNTP | Video signal trailing edge pulse |

Another item that should be noted, since it will be helpful in understanding the present device, is that normally the expression "video signal" means a signal which is modulated to represent different degrees of black and white. In the present device, the "video signal" simply represents a time position when the bottle is being scanned and hence it is all black and there are no degrees of black and white. In short, the output signal from the TV camera is either completely black or completely white as far as the present system goes.

Figure 3:
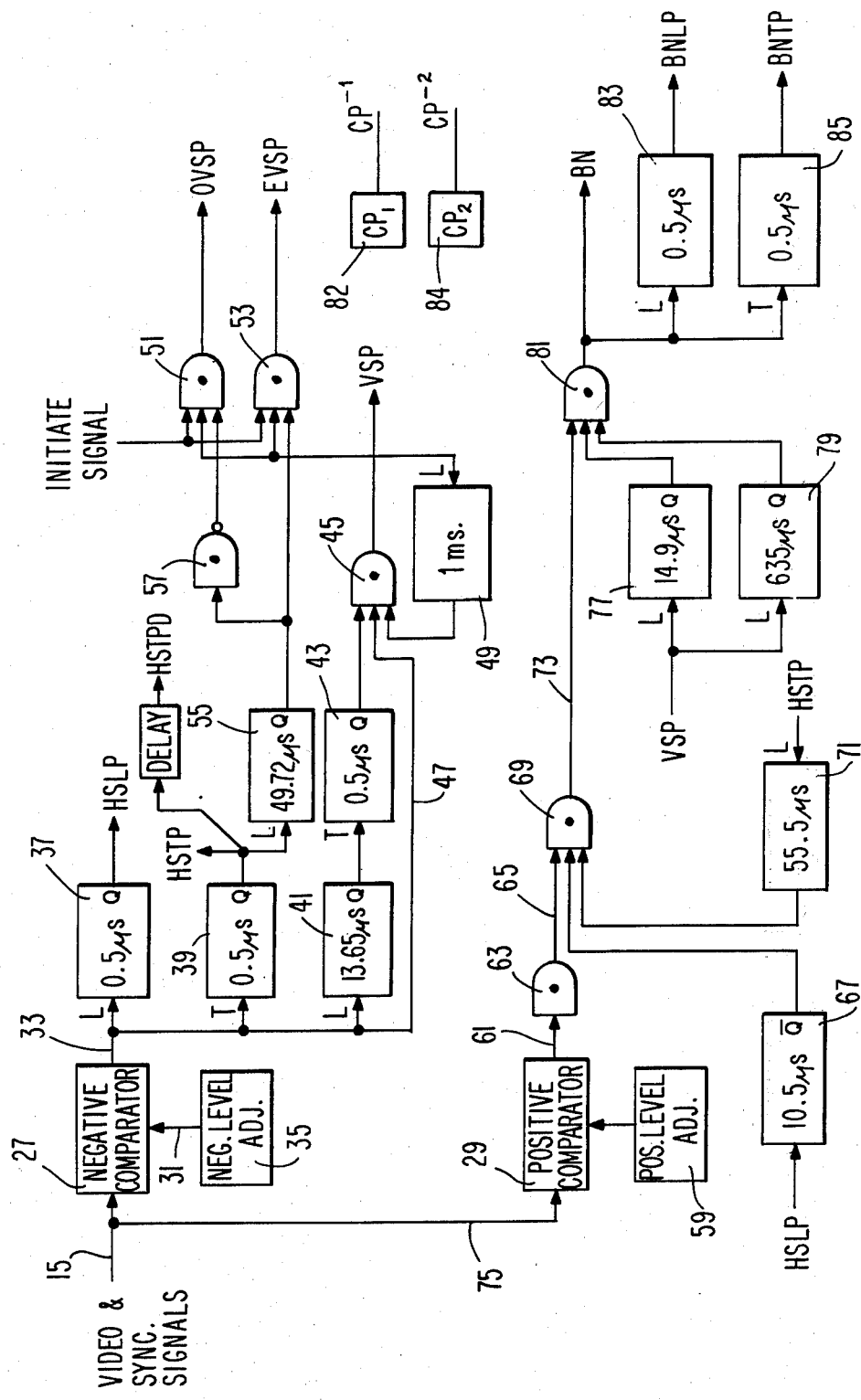
FIG. 3 is a logic diagram showing the electronic circuitry required to produce the basic control signals rom the TV camera output.
Figures 10, 11:
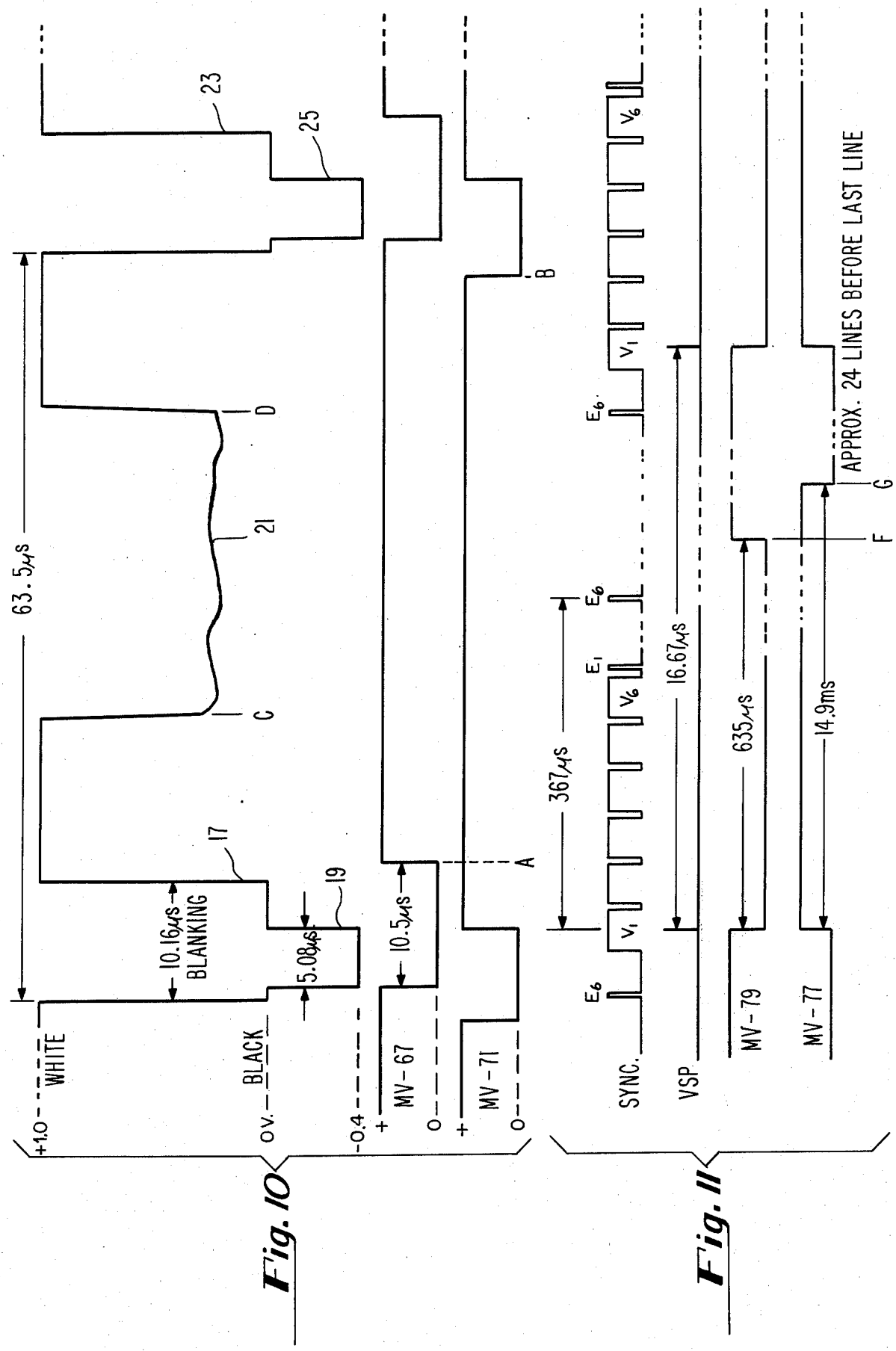
FIG. 10 shows the relationship between the video signal and certain other necessary timing signals.
FIG. 11 is a further timing signal showing the relationship between other necessary timing signals used with this system.

Bearing the above concepts in mind, consider FIG. 3 wherein we find the logic circuitry for producing the signals shown in above table. At the left-hand most side there is an input cable 15 from the TV camera and there are video signals plus sync signals transmitted on that cable. If we examine FIG. 10 we find a small portion of the signal which is transmitted on the cable 15. In FIG. 10, the upper graph, shows a blanking pulse 17 with a horizontal sync pulse 19 superimposed thereon, a video signal 21, a second blanking signal 23 and a second horizontal sync pulse 25 superimposed on the second blanking signal. The signals from the TV camera are as shown in FIG. 10; i.e., the sync pulse is negative and the video signals are positive with respect to a zero reference. In the present device, the bottle is seen as a black silhouette on a white background. The signal corresponding to the white background has a positive polarity and an amplitude of approximately one volt.

The signal which corresponds to the bottle, as can be seen in FIG. 10, is somewhere in the range of 0.2 to 0.3 volts. As also can be determined from FIG. 10, the horizontal sync pulse is a negative pulse.

In view of the polarity of the information signals appearing on cable 15, the circuitry of FIG. 3 first provides a negative comparator device 27 and a positive comparator device 29. The negative comparator may be a Model No 711 manufactured by Signetics, Inc. and serves to only transmit therethrough signals which are below a certain negative level. The reference for the "certain negative level" is transmitted on line 31 from the negative level adjustment device 35. The negative level adjustment device may be a simple decade resistor box connected to the power source which provides a signal to the negative comparator 27 so that the only signals which are transmitted from the output of the negative comparator 27 are signals which are more negative than some particular level.

In the present device, the negative level is chosen as −0.25 volts and therefore (as can be determined from FIG. 10) the only pulses which appear on line 33 are the horizontal sync pulses. It should be borne in mind that the equalizing pulses and the vertical sync pulse also appear on line 33, but they appear during a time that the scan is not looking at the bottle.

The negative comparator operates such that when the potential on line 15 becomes more negative (about 5 mv) than the reference potential on line 31, the output signal on line 33 switches from low ($-1.0$ V approximately) to high ($+4.0$ V approximately). Therefore the horizontal sync pulses appear on line 33 as positive signals. The positive horizontal sync pulses are transmitted to the one-shot multivibrator 37 which only responds to a positive going excursion and is turned on for approximately 0.5 microseconds. Accordingly the output from the one-shot multivibrator 37 is a horizontal sync leading edge pulse because it responds to the leading edge of the horizontal sync pulse. The HSLP pulse can be seen in FIG. 8 and it will be noted thereat that the width of the pulse is quite narrow.

The horizontal sync pulses are also transmitted to the one-shot multivibrator 39. Now the one-shot multivibrator 39 only responds to a negative excursion and the negative excursion only occurs at the trailing edge of the horizontal sync pulse, therefore the output of the one-shot multivibrator 39 is a horizontal sync trailing edge pulse.

It should be understood that the multivibrators 37 and 39 can be a standard one-shot multivibrator such as Model 74123 manufactured by Signetics, Inc.

The horizontal sync pulses are also transmitted to the one-shot multivibrator 41. The one-shot multivibrator 41 is turned on for 13.65 microseconds and only responds to a positive excursion. Therefore the output of the one-shot multivibrator 41 is a gate signal that is 13.65 microseconds long and which commences with the leading edge of the horizontal sync pulse. The output from the one-shot multivibrator 41 can be seen in FIG. 8.

Figure 8:
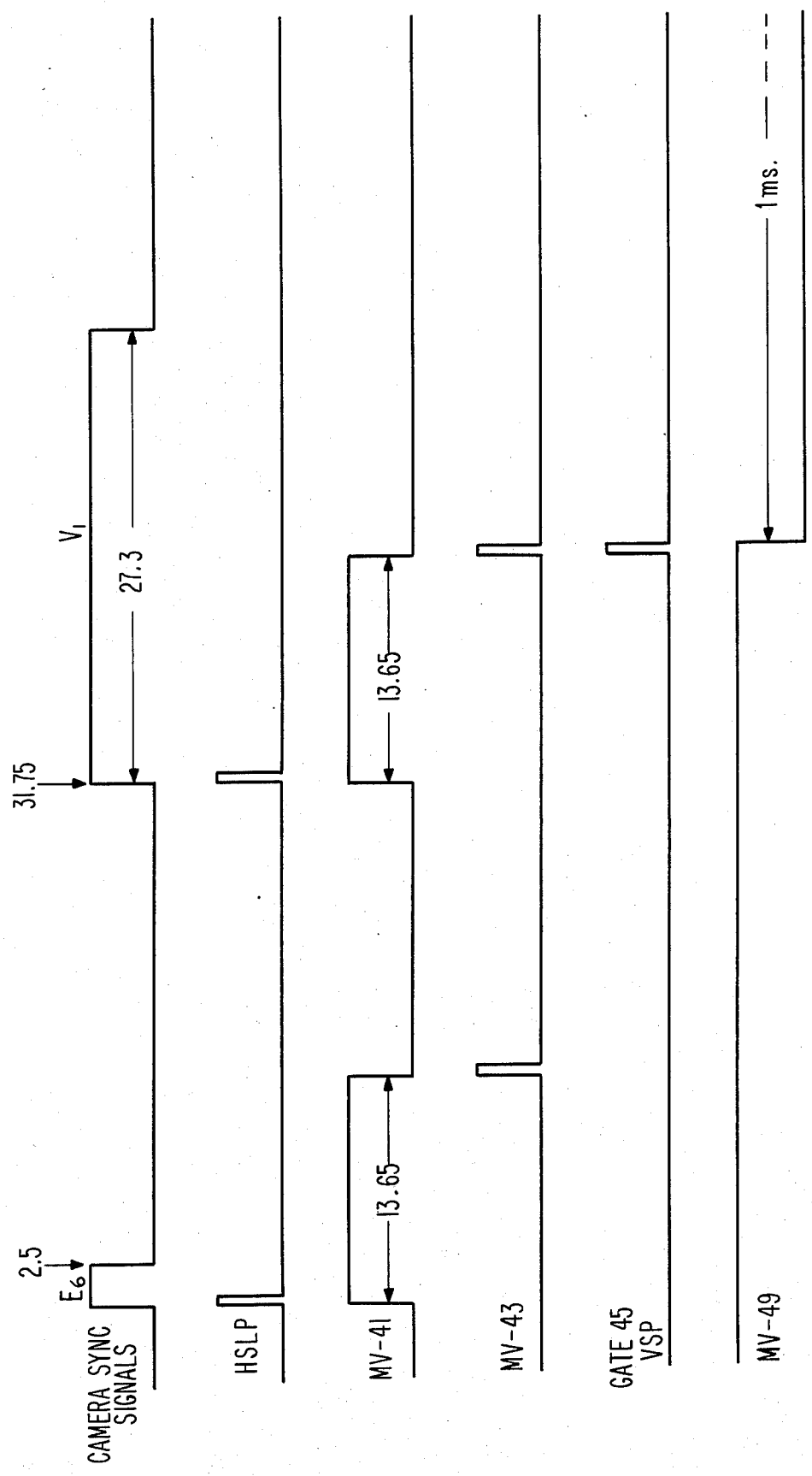
FIG. 8 is a timing diagram showing the relationship between various timing signals.

It will be noted that the output from the one-shot multivibrator 41 is transmitted to a second one-shot multivibrator 43 which is turned on for 0.5 microseconds and only responds to a negative excursion. In short the output from the one-shot multivibrator 43 is a narrow pulse which starts at the time the gate signal from the one-shot multivibrator 41 is experiencing a negative excursion or is ending. The relationship between the output of the one shot multivibrator 43 and the one-shot multivibrator 41 can be seen in FIG. 8. The output of the one-shot multivibrator 43 is transmitted to the AND gate 45. The AND gate 45 needs a high signal on each of its input lines to provide a high signal on its output line. From the relationship in FIG. 8, it can be seen that the output from the one-shot multivibrator 43 coincides with a high signal on line 47 during the vertical sync pulse interval $V_1$. The vertical sync pulses are generated by the TV camera. The output from the one-shot multivibrator 49 is normally high as can be seen in FIG. 8 and therefore during the vertical sync pulse interval, the AND gate 45 provides an output which coincides with the output from the one-shot multivibrator 43. The output from the AND gate 45 is the VSP signal which is transmitted to numerous places as will become apparent hereinafter.

Initially the VSP signal is transmitted to the AND gates 51 and 53. The VSP signal is also transmitted to the one-shot multivibrator 49 to turn that multivibrator on for 1 millisecond. When the multivibrator 49 is turned on for the 1 millisecond, the AND gate 45 cannot be turned on, and this relationship is apparent in FIG. 8. The purpose of MV49 is to assure that only the first VSP, as shown in FIG. 11, passes through gate 45. Before we consider the input signals and AND gates 51 and 53 we must consider the output signal from the one-shot multivibrator 55.

Figure 9:
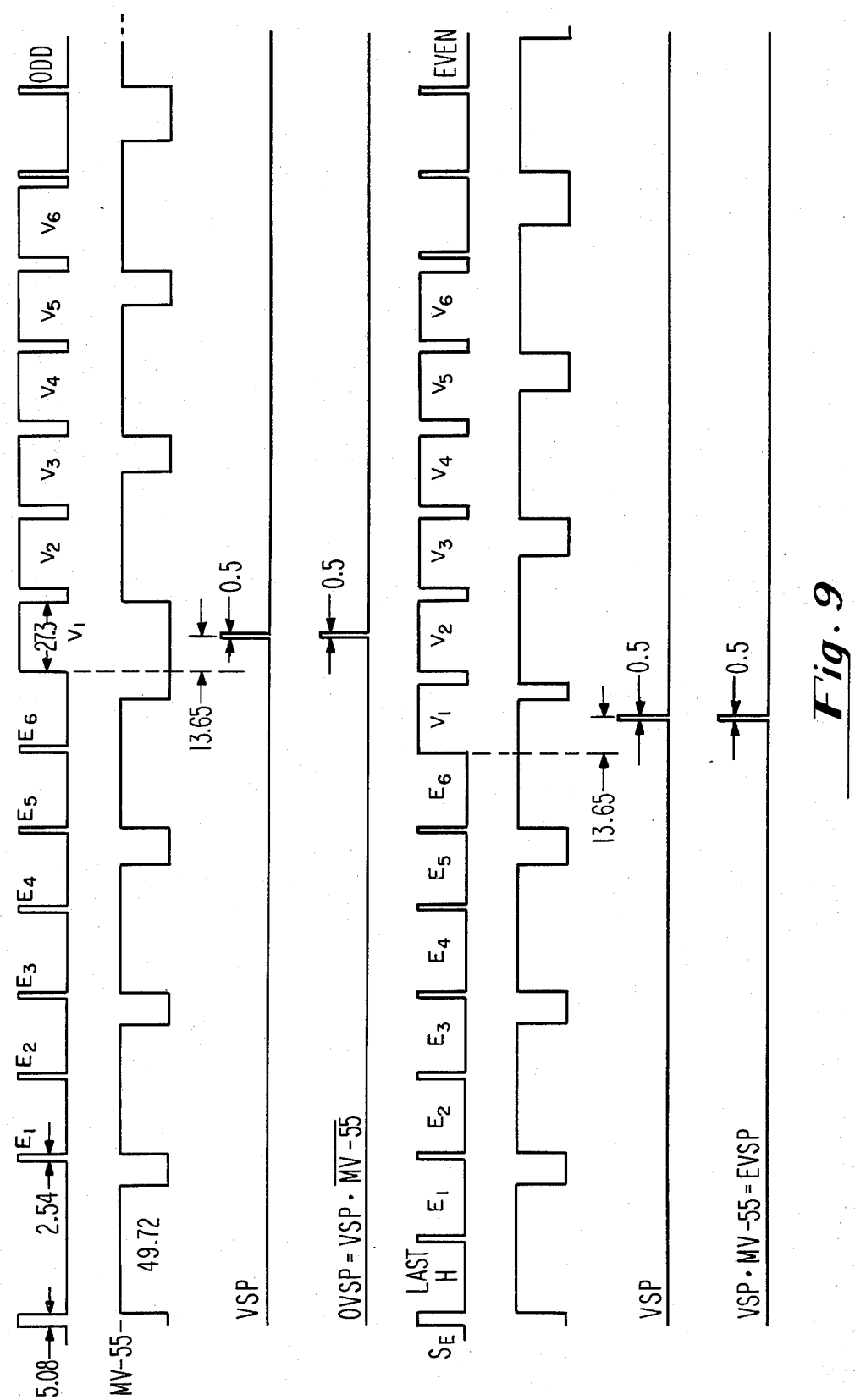
FIG. 9 is a second timing diagram also showing the relationship between a number of necessary timing signals.

The HSTP signal which is the output of the one-shot multivibrator 39 is transmitted to the one-shot multivibrator 55 which is non-retriggerable. Multivibrator 55 can be Model 74121 manufactured by Signetics, Inc. The one-shot multivibrator 55 responds to a positive excursion and therefore is turned on by the leading edge of the horizontal sync trailing edge pulse. The one-shot multivibrator 55 is turned on for 49.72 microseconds. The relationship between the trailing edge of the horizontal sync pulses and the gating signals produced by the one-shot multivibrator 55 can be seen in FIG. 9. The gate signal from the one-shot multivibrator 55 is transmitted to the inverter 57, which inverts the signal and provides a negative gating signal to the AND gate 51. Accordingly, it becomes apparent that when the one-shot multivibrator 55 is not producing an output, the output from the inverter 57 will be high to partially condition the AND gate to provide an output signal. The initiate signal provides the third input signal to the AND gate 51 to produce the OVSP signal. The initiate signal is generated by the bottle passing in front of a photocell beam to generate a signal indicating that a bottle is entering the read station. The photocell signal sets a flip-flop whose output from the set side is connected to an AND gate. The other input to the AND gate is a vertical sync pulse. The output from the AND gate sets a second flip-flop whose set side output is the initiate signals. These last two described flip-flops are reset by the succeeding vertical sync pulse. The relationship of the OVSP signal can be seen in FIG. 9. In FIG. 9 it will be noted that in order to generate an OVSP there must be a VSP signal and the output from the one-shot multivibrator 55 must be low.

The AND gate 53 also has a VSP signal as one of its signals and an initiate signal as one of its input signals. The difference between the inputs to the AND gate 51 and to the AND gate 53 is that the AND gate 53 responds when there is an output from the one-shot multivibrator 55. This relationship can be seen on FIG. 9.

The OVSP signal is VSP of the odd field and EVSP is the VSP of the even field.

Thus far we have considered the generation of the HSLP signal, the HSTP signal, the VSP signal, OVSP signal, and the EVSP signal.

The positive comparator device 29 is the same as the negative comparator device but is used in positive comparison made. A positive level signal is transmitted thereto from the positive level adjustment device 59. The positive level adjustment device 59 can also be a decade box or some other device which will simply transmit a certain voltage level to act with the positive comparator. The positive comparator 29 will provide an output signal if its input is in excess, in the positive polarity sense, of the positive level provided by the positive level device 59. In the preferred embodiment, the positive level is 0.5 volts. Now if we look at FIG. 10, it can be seen that only the white signal will be greater than 0.5 volts and therefore there will be an output from the positive comparator when the background of the bottle is being scanned and not when the bottle is being scanned. In other words, when the TV camera sees the white background of the screen, a positive signal is transmitted on line 61. This positive signal on line 61 is transmitted to the inverter 63 whereat it is inverted into a negative signal. Accordingly then the only time there is a positive signal on line 65 is when the TV camera is seeing either video or as seen in FIG. 10 when the blanking signals are occurring.

In order to keep the system from being confused with respect to the horizontal blanking signals, the one-shot multivibrator 67 provides an input to the AND gate 69 and the one-shot multivibrator 71 provides an input to the AND gate 69. The relationship between the outputs of the one-shot multivibrators 67 and 71 can be seen in FIG. 10. The one-shot multivibrator 67 is turned on in response to an HSLP signal and the output goes low for some 10.5 microseconds. On the other hand, the one-shot multivibrator 71 is turned on in response to the trailing edge of the horizontal sync pulse and its output goes high, or positive, for some 55.5 microseconds. Accordingly, as can be seen from FIG. 10, one or the other of the outputs from the one-shot multivibrators 67 and 71 is negative during the entire period that the blanking signal is in effect so that while there may be a positive signal on line 65, the AND gate 69 will not be fully conditioned until the outputs from both the one-shot multivibrator 67 and 71 are both high, or positive.

Accordingly then the multivibrators 67 and 71 remove the confusion from the system related to the horizontal blanking pulses. However, the TV camera provides vertical blanking signals as well as the horizontal blanking signals. These vertical blanking signals pass through the AND gate 69 and would confuse the system because it would appear as a video signal. In order to eliminate any confusion to the system with respect to the vertical blanking signals, the one-shot multivibrator 77 and the one-shot multivibrator 79 are employed. The one-shot multivibrators 77 and 79 are turned on by the VSP signal whose generation we have just discussed. The relationship between the one-shot multivibrator 77 and the one-shot multivibrator 79 and the VSP signals can be seen on FIG. 11. It will be noted that the output from the one-shot multivibrator 79 is low in response to an input signal while the output from the one-shot multivibrator 77 is high in response to an input signal. It will be also noted that the one-shot multivibrators 77 and 79 respond to a positive excursion or the leading edge of the VSP signal.

As can be seen in FIG. 11 when the VSP signal is generated, the output from the one-shot multivibrator 77 goes positive, or high, for 14.9 milliseconds while the output from the one-shot multivibrator 79 does low, for 635 microseconds. The AND gate 81 (FIG. 3) responds to positive input signals and hence from FIG. 11, it can be seen that the only time the AND gate 81 can be fully conditioned is between the points F and G. It will be noted in FIG. 11 that the output from the gate 77 is shown partially as a dashed line and actually the time between the points F and G is some 14.3 milliseconds long which is sufficient time to have the TV camera scan the bottle.

Accordingly, then, the output from the AND gate 81 is the true video signal BN. Actually the BN signal will be a long gate pulse because, as explained earlier, it is simply the signal which indicates that the camera is not looking at the white background and is not a signal in the true video sense that it is proportionally black and white. Since the BN signal is a gate-type signal, it will have a leading and a trailing edge. The video signal BN is transmitted to the one-shot multivibrator 83 which responds to a positive excursion and produces the BNLP signal while the BN signal is also transmitted to the one-shot multivibrator 85 which responds to a negative excursion and provides the BNTP signal.

It should be further noted in FIG. 3 that there are two clock pulse generators 82 and 84. Clock pulse generator 82 provides CP-1 pulses at a rate of 5 MHZ in the preferred embodiment, while clock pulse generator 84 provides CP-2 pulses at a rate which is determined by the speed of the conveyor.

Thus far we have considered the generation of the BN signal, BNLP signal, and the BNTP signal as well as the other control signals mentioned in connection with the study of FIG. 3.

Figure 2:
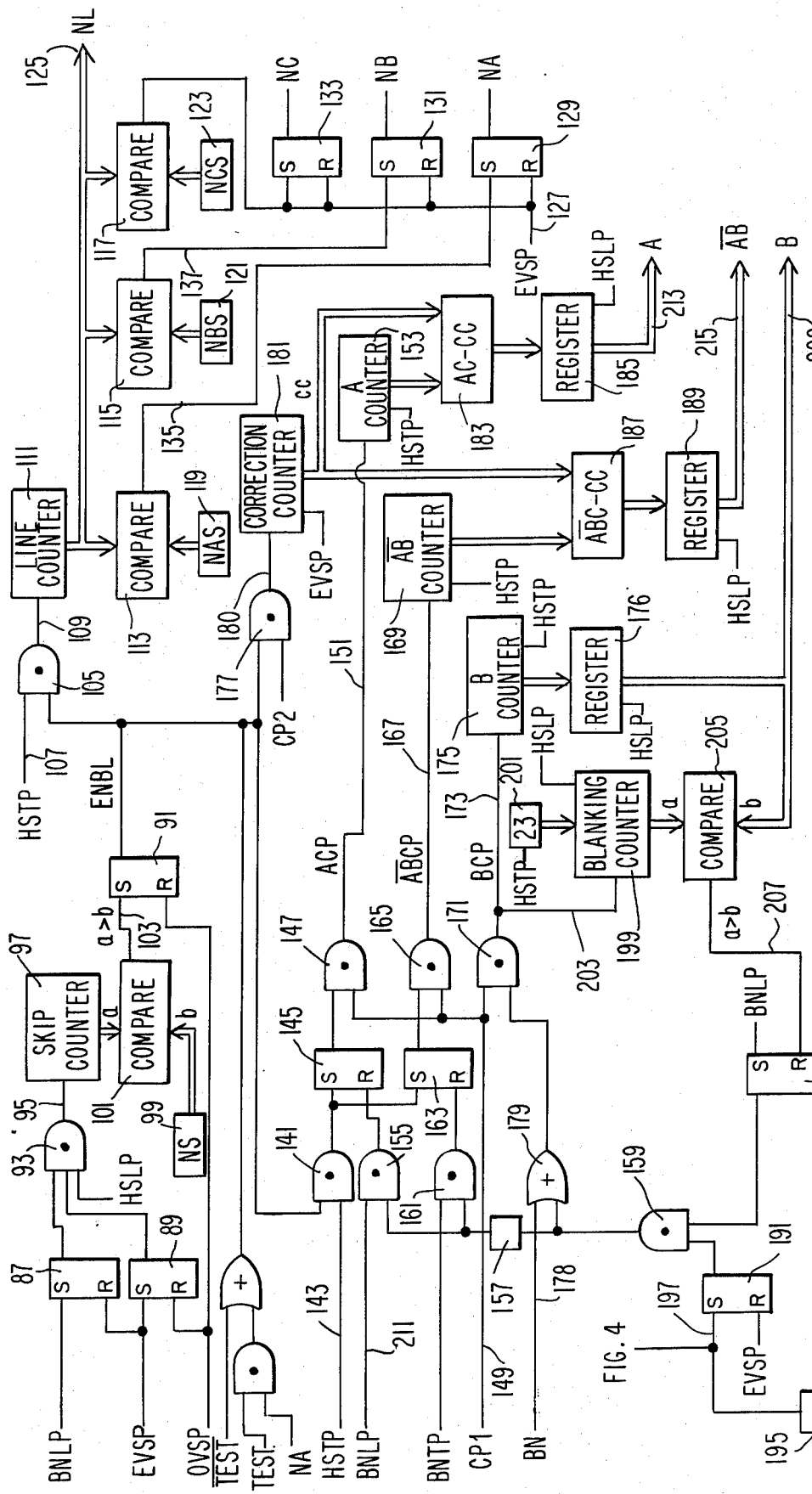
FIG. 2 is a schematic diagram of the logic circuitry employed to convert the video signals into digitized signals and thereafter into control signals.

Consider now FIG. 2 which shows the logic circuitry required to generate the signals that we discussed earlier in connection with FIG. 1.

It should be borne in mind that the system as mentioned earlier operates in two distinct modes. In the first mode of operation, it records information from a standard, or acceptable bottle. In the second mode of operation, the system scans or examines electronically a hot bottle and compares its parameters with the information that was obtained from the standard bottle.

First let us consider that the system is going through the procedure of scanning a standard bottle and recording the information to be used thereafter with scans of "hot" bottles.

The standard bottle is taken on a conveyor or simply placed in the reading station. When the system is turned on and is operating, the TV camera will start scanning the screen against which the standard bottle is silhouetted and the first scans will be above the bottle and therefore only the white background of the screen will be seen by the TV camera. Indeed if the TV camera should start its scan with an odd line scan, the OVSP signal would be generated and this would reset the flip-flop 89 as well as the flip-flop 91. Accordingly there would be no enable signal generated as will become apparent hereinafter. On a succeeding scan of the EVEN line the EVSP signal will be generated as previously described and this signal will serve to set the flip-flop 89 and re-set the flip-flop 87. Now, if during the initial part of the EVEN scan, the bottle does not come into a position where the TV camera sees the bottle, then there will be no BNLP, no video signal generated, and hence the flip-flop 87 will not be set. Eventually the TV scanning operation will come down to a point where it just scans or strikes the top of the image of the bottle and this will provide a BNLP signal, as described earlier, which will set the flip-flop 87. Now it should be understood that while the present description suggests that the meaningful information is determined during the EVEN scans, the system can operate whereby the first vertical sync pulse, irrespective of whether it is ODD or EVEN is accepted as ODD and is used to reset flip-flops 89 and 91 and this same vertical sync pulse delayed is used as the EVSP. Thereafter the system would perform the check as described herein and it would make no difference whether the meaningful information was obtained by ODD or EVEN scans.

With the flip-flops 89 and 87 set, two of the inputs to the AND gate 93 will be high. The scan which hit the top of the bottle was started with a horizontal sync pulse and so the HSLP signal to AND gate 93 will also be high and hence the AND gate 93 will be fully conditioned when the first video signal is generated. In other words, as soon as the TV camera sees the topmost part of the bottle, the AND gate 93 will be fully conditioned to transmit a signal on line 95 to the Skip Counter 97. It should be recalled that the EVSP signal is generated during the first vertical sync pulse from the TV camera and there will be some 250 or more horizontal sync pulses before the next vertical sync pulse period occurs and hence before the next $V_1$ signal (FIG. 8) is generated, so that the OVSP signal will not reset the flip-flop 89 for a relatively long period of time. Accordingly there may be some 250 scans depending upon which scan first sees the top of the bottle; but under any circumstances, the output from the flip-flops 87 and 89 will be high for a large number of scans and therefore for a large number of horizontal sync pulses. Accordingly there is an output signal on line 95 every time there is a horizontal sync pulse from the TV camera. In effect the Skip Counter 97 counts horizontal sync pulses which is analogous to counting lines because each scanning line is started by a horizontal sync pulse.

The Skip Counter 97, as its name indicates, is for the purpose of enabling the system to skip examining a certain number of lines. The system takes into account that when the TV camera initiates scanning and, in fact, actually starts "seeing" the bottle, the very edge of the bottle may not provide suitable contour information. In the preferred embodiment, the system skips the first line and hence the value of one is set into the skip switch 99 and this value is sent to the compare device 101. The compare device 101 is an ordinary comparison circuit such as Model 7485, manufactured by Signetics, Inc. When the count in the Skip Counter 97 has exceeded the count entered from the NS Switches 99, then a signal is transmitted on line 103, that signal indicating that the Skip Counter value is greater than the value from the switch 99. The reason that the signal on line 103 is only transmitted when the Skip Counter is greater than the value from the NS switch 99, rather than simply equal to the value of switch 99, is that when the system initially starts up, it is conceivable that the values could be equal and then an enable signal would be generated and that would be undesirable.

Skip counter 97 is reset to zero by means not shown, prior to the time that a new bottle is to be scanned. The reset pulse comes from EVSP.

The signal on line 103 sets the flip-flop 91 and the output from the flip-flop 91 is an Enable Signal. This Enable Signal is the signal that actually basically starts the system in its many counting procedures to examine the bottle or to generate the values NA, NB, NC and ND as shown in FIG. 1.

The Enable Signal is transmitted to the AND gate 105 and the first horizontal sync trailing pulse after the last line has been counted by the Skip Counter will be transmitted on line 107 to fully condition the AND gate 105. Bear in mind that the line 107 will receive every horizontal sync trailing edge pulse, but it is only the horizontal trailing sync edge pulses which occur after the Skip Counter has counted the selected number of lines that are to be skipped that becomes meaningful. The first horizontal trailing edge pulse after the Skip Counter has counted its selected number of lines, will provide an output on line 109 and that output will be counted as the first line in Line Counter 111. Every horizontal trailing edge pulse thereafter for as long as the Enable Signal is present will be transmitted through the AND gate 105, on line 109 to be counted in the Line Counter 111.

The Line Counter 111 is an ordinary 8-bit binary counter and it accepts pulses from the AND gate 105, counts these pulses and provides an 8-line parallel output to three compare units 113, 115 and 117.

The system takes into account that the symmetry test, or the test for the flatness of the top of the bottle, can be accomplished by the time that the TV camera has scanned through the NA position shown in FIG. 1. The NA position will represent a certain number of lines and this will depend upon the size and position of the bottle. Accordingly, that number of lines is set up in a series of switches in the NAS box 119 and the value is transmitted into the compare unit 113. It should be understood that while the system shows switches, other forms of devices for entering information could be used.

In the same way, the user of the system knows that he can accomplish the measurement of the thread width by the time the scan reaches the NB position, shown in FIG. 1, and this, too, represents a certain number of lines. Accordingly the NB value or the number of lines counted to get to the NB position is set into the NBS switch box 121 and that value thereafter is transmitted into the compare unit 115. The philosophy for determining NC is somewhat different from the philosophy for determinig NA and NB. The user wants to know when NC occurs because it is after the occurrence of the NC position that he wants the system to next look for an A min". in particular the "A min" shown at the ND position in FIG. 1. The user knows that the NC position will occur by a certain number of lines and he enters the value for that number of lines in the NCS box 123 (switch box). Thereafter that value is transmitted to the compare unit 117.

Finally it will be noted that the Line Counter transmits the number of lines that it has recorded to an output position 125 and that NL signal is used as will be explained hereinafter.

The compare units 113, 115 and 117 are similar to the compare unit 101 and are well known in the art.

It will be recalled that we started to generate the Enable Signal initially by setting the flip-flop 89 and resetting the flip-flop 87 with the EVEN vertical sync pulse. That same EVEN vertical sync pulse was transmitted on line 127 to reset the flip-flops 129, 131 and 133.

Now as the horizontal sync trailing edge pulses appear on line 107 and provides a count for the lines that the TV camera is employing to scan the bottle, these counts are transmitted simultaneously to the compare units 113, 115 and 117. When the value of the Line Counter III equals the NA value which has been placed in the switch box 119, there will be an output signal on line 135 which will set the flip-flop 129 and produce an NA signal. In like manner when the count in the Line Counter III equals the value of NB set in the NBS switch box 121, there will be an output from the comparator 115 on line 137 which will set the flip-flop 131 to provide an NB signal. In addition when the Line Counter III counts the number of lines that equals the NC value placed in the NCS switch box 123, there will be an output from the comparator 117 which will set the flip-flop 133 to produce the NC signal. The use of the NA, NB and NC signals will become apparent hereinafter. In any event it becomes apparent that the system knows when to end the symmetry check (by the generation of the NA signal), when to terminate the thread width examination (by the generation of the NB signal), and when to start looking for the second meaningful "A min" (because of the generation of the NC signal). The Line Counter III is reset prior to examining a new bottle. The reset signal is generated by the EVSP signal. It will be recalled that earlier in the discussion, we dealt with the problem of determining the value of A, the value of $\overline{AB}$ and the value of B as shown in FIG. 1. It should also be recalled that in connection with our discussion of FIG. 10, that the system actually sees a white signal, or a black signal, and both of the signals have meaning insofar as they are present for a period of time. This, of course, represents an analog type signal and the system is designed to convert such analog signals into digital values and in particular into digital values representing A, $\overline{AB}$ and B. Accordingly let us look at FIG. 2 with respect to generating the A value in digital form.

If we also look at FIG. 1, it becomes apparent that we want to generate the A value starting with the initial part of the scan and we have already determined that we are only interested in lookin at the video scan after we have skipped a certain number of lines. These considerations were taken into account when we generated the Enable Signal from the flip-flop 91. The Enable Signal is transmitted to the AND gate 141. The other input to the AND gate 141 is the HSTP signal transmitted on line 143. The HSTP signal, transmitted on line 143, is the same HSTP signal which was transmitted on line 107 to start the Line Counter III into operation. Accordingly at the first scan, after the Enable Signal has been generated, the flip-flop 145 will be set and its output will be transmitted to the AND gate 147.

Now it will be recalled when we considered FIG. 3 that the clock pulse generator 82 generated the CP-1 signals at the 5 MHZ rate. The CP-1 signals are transmitted on line 149 to the AND gate 147 and hence there are pulses (ACP) produced on lone 151 to be counted to represent the digitized value of the parameter A, as shown in FIG. 1.

The same HSTP signal which was transmitted as an input to the AND gate 141 is also transmitted to the A counter 153 to reset that counter to zero. Accordingly, the CP-1 pulses which come through the AND gate 14 as ACP pulses on line 151, are counted by the A counter 153. Now as can be seen in FIG. 1, the system wants the A value to be determined as of when the scan reaches the leading edge of the bottle. When the scan reaches the leading edge of the bottle, there will be a BN signal generated which we discussed in connection with FIG. 3. The BN signal represents the video signal and it will be recalled that this signal is a gate signal and that we generated a BN leading edge pulse (BNLP). The BNLP is transmitted to the AND gate 155 whose other input is from the inverter 157. The input to the inverter 157 is from the AND gate 159 whose input we will deal with hereinafter. For the moment, assume that the output from the AND gate 159 is low and therefore the output from the inverter 157 is high so that the AND gate 155 is conditioned to pass the BNLP signal when it is generated. Accordingly when the TV camera sees the leading edge of the bottle and the BNLP signal is generated, there is an output from the AND gate 155 to reset the flip-flop 145. When the flip-flop 145 is reset, there will no longer be a signal to condition the AND gate 147 to pass the CP-1 pulses. Hence the CP-1 signals will no longer be transmitted to the counter 53. Accordingly the count in the counter 153 represents the value of A. This count may have to be modified, as will be discussed hereinafter; but for the moment, we will accept the proposition tha the value of A, as shown in FIG. 1, has been counted or determined in the A counter 153.

If we examine FIG. 1 we find that if we want to get the value of $\overline{AB}$, the system must start counting the CP pulses at the beginning of the scan and stop counting those CP pulses when the scan reaches the trailing edge of the bottle; i.e., stop counting at the end of the video signal.

The same output signal from AND gate 141 that turned on the flip-flop 145 also turns on the flip-flop 163. When the flip-flop 163 is turned on, it conditions the AND gate 165 to pass the CP-1 signals as $\overline{AB}$CP signals and hence we have signals on line 167 that represent the $\overline{AB}$ count. The reason that the signals on line 167 represent the $\overline{AB}$ count, as opposed to the signals on line 151, representing the A count is because the signals on line 167 get terminated at a different time than the signals on 151. It will be recalled that when we studied FIG. 3, we generated a BNTP pulse which represents the video trailing edge pulse, or stated another way, represents the pulse that occurs when the camera sees the right-hand end of the bottle. The output from the inverter 157 conditions the AND gate 161 to pass the BNTP pulse in the same way that the ouput from the inverter 157 conditioned the AND gate 155 to pass the BNLP pulse. When the BNTP pulse passes the AND gate 161, it resets the flip-flop 163 to terminate the ABCP pulses which are transmitted to counter 169.

Accordingly, when the video signal terminates and there are no longer any pulses on line 167, it can be assumed that the number of CP-1 pulses recorded in the $\overline{AB}$ counter 169 is the $\overline{AB}$ value. As was mentioned in connection with the value of the A counter 153, the value in the $\overline{AB}$ counter 169 may be subject to a correction. The same HSTP signal which reset the counter 153 also resets counter 169.

If we once again examine FIG. 1 we recognize that we want to determine the value of B and that B value is simply representative of the video signal or time that the scan is actually looking at the bottle.

As can be seen in FIG. 2, the CP-1 pulses are also transmitted to the AND gate 171 and the output signals from the AND gate 171 appear on line 173 as BCP signals to be transmitted to the B counter 175. Inasmuch as we need to pass the BCP signals along line 173 during the time that the video signal is being generated, we find we have a BN signal transmitted on line 178 to the OR gate 179, to fully condition the AND gate 171 as long as the video signal is being generated. The other input to the OR gate 179 will be discussed hereinafter.

Accordingly the CP-1 signals are transmitted through the AND gate 171 as BCP signals as long as the video signal is present and are transmitted to be counted in the counter 175. The counter 175 is reset to Zero with the same HSTP signal as reset the counters 153 and 169. Accordingly, when the video signal ends, the AND gate 171 will no longer be fully conditioned to pass the CP-1 pulses and hence the count in the counter 175 will be the value of the parameter B, shown in FIG. 1.

There are two phenomena which take place in connection with the present system which cause the system to introduce correction features in order that the values of A, $\overline{AB}$ and B actually represent the measurements shown in FIG. 1. It should be recognized that the bottle is on a conveyor belt and will be moving while it is in the reading station. In one mode of operation, the image is received by the TV camera instantaneously because of a flash from a flash gun; but in the other mode of operation, wherein the bottle is passed in front of a screen, as previously described, the system has to take into account that for each instant of the scan the bottle is in a somewhat different position. To clarify this concept somewhat, consider that the bottle, whose upper portion is shown in FIG. 1, is moving from left to right. If that were the case, the value of "A min" for some instant in time would not be the same value of "A min" in the next instant of time because the bottle would have moved somewhat to the right. Accordingly as was mentioned in our study of FIG. 3, the system provides a clock pulse generator 84 which generates a clock pulse that is commensurate with the speed of the conveyor belt. The CP-2 pulses from the clock pulse generator 84 are transmitted to the AND gate 177. The AND gate 177 has been partially conditioned by the Enable Signal so that the CP-2 pulses which fully condition the AND gate 177, are transmitted on line 180 to the correction counter 181. The correction counter 181 has been reset by the EVSP signal. Accordingly once the Enable Signal has been generated, and the bottle, of course, is moving on the conveyor belt, the CP-2 pulses are counted by the counter 181. At the end of a given scan, there will be a value of A, counted in the counter 153, as described previously, and there will be a value for the correction factor counted in the counter 181. These two values are transmitted to the subtract circuit 183, wherein they continually effect a subtraction of the two values being entered. The output circuitry from the subtract circuit 183 comprises eight parallel lines which go to the register 185. At the beginning of the next scan, the final quotient (the corrected value of measurement A) is gated into the register 185 by the HSLP signal of the next scan. The substract circuit 183 is actually an adder circuit and accomplishes substraction by using the complement of the subtrahend. The subtract circuit 183 is a Model 7483 manufactured by Signetics, Inc.

If we look at FIG. 1, we can readily determine that the $\overline{AB}$ count would also change because of the movement of the bottle, hence the correction count is transmitted from the counter 181 to the subtract circuit 187. The information in the counter 169 which represents the $\overline{AB}$ value, as well as the correction factor in the counter 181 continually effect a subtraction in the subtraction circuitry 187, while the values in the counter 169 and 181 are changing. At the end of the scan, when the value of the signals in the subtraction circuit 187 represents the correct quotient, or correct value of $\overline{AB}$, these signals are transmitted to and accepted by the register 189 in response to an HSLP signal which takes place at the beginning of the next scan.

Accordingly, the A value and the $\overline{AB}$ value hve been corrected for the movement of the conveyor belt. It should be noted that if the flash technique is used, the correction circuitry is not necessary.

As mentioned earlier, there is a second problem for which the system must compensate. It has been determined that the bottle, or at least a portion of the bottle, acts as a lens for the light from the screen which stands behind the bottle. Accordingly, in the middle of the bottle, as considered from left to right and as considered from top to bottom, there very often appears a white lighted streak. If the TV camera is scanning the bottle and sees this vertical streak of white light, it will stop producing a video signal until that band of white light has been passed over, at which time the video signal will recommence. For the purposes of the present system, the video signal should continue as long as the TV camera is scanning the bottle, or "seeing" the bottle. Hence, the system must take into account that the lens phenomena of the bottle may be in effect and eliminate the spurious signals which would occur if the camera were to see the white streak of light resulting from the lens effect. It has been determined that the lens effect does not take place before the twelfth line of the scanning operation, and does not locate itself near the right-hand end of the bottle. Philosophically, the system is designed to blank out the video control signals in the middle ofthe bottle, permit the CP-1 signals to continue to generate pulses as though the video signal were still turned on, and enable the video signal to take control before the scan reaches the right-hand end of the bottle.

The foregoing goals are attained in the following manner. There is a flip-flop 191 (in the lower left corner of FIG. 2) which is reset with the same EVSP signal which we considered earlier in connection with generating the Enable Signal. Accordingly, this flip-flop provides no output from its set side in the initial part of the scanning operation. The value 12 is fed into the switch in the switch box 193 and that value is transmitted to the compare circuit 195. The compare circuit 195 is the same as the compare circuits 113, 115 and 117. The other input to the compare circuit is the NL signal generated on channel 125 and, hence, when the NL value gets to the value 12, there is a signal transmitted on line 197. This signal sets the flip-flop 191; hence there is a high signal to the AND gate 159. This information signal will take care of the condition that the video will be relieved of its control function only after the scan has reached line 12, thereby preventing it from interfering with the symmetry check.

It will be noted that there is a blanking counter 199 which is reset with an HSLP signal. There is an input from the "23" switch box 201 to the blanking counter 199 in order to jam the value "23" therein. The value "23" is set in the switch box 201 and is gated into the blanking counter by the HSTP signal. It should be understood that values other than "23" can be used. A further input to the blanking counter are the BCP signals from the AND gate 171 which are transmitted on line 203. Accordingly at the beginning of the scan, the value "23" is jammed into the blanking counter 199 and the first B count which comes through, after the video signal has been generated, advances the blanking counter 199 to the count of 24 and so on. The value of the blanking counter 199 is compared against the value of the last B count from the previous scan and the comparison is made in the comparator circuit 205. To state the foregoing another way, a B count has been registered from a previous complete scan; i.e., a plurality of horizontal scans, and that B count was transferred to the register 176, in response to the HSLP signal which reset the blanking counter 199. The B counter 175 is reset by the HSTP pulse which transferred the value "23". The B count in the register 176 is transmitted to the compare unit 205 whereat it is compared against the value in the blanking counter 199. The value of the B count, as held in register 176, is initially always higher than the value of the blanking counter which is just commencing a new scan. It is only when the value in the blanking counter exceeds the value in the register 176 that there is an output signal on line 207. This will occur when the current scan is approximately 23 pulses from the end of the bottle. When the value in the blanking counter exceeds the value of the register 176 the output signal from the compare circuit 205 will reset the flip-flop 209.

Flip-flop 209 is set by the BNLP signal as soon as the video signal from the TV camera is generated. Accordingly, the output from the flip-flop 209, in conjunction with the output from the flip-flop 191, fully condition the AND gate 159, and this provides a high signal to the OR gate 179.

Let us consider the meaning of the inputs to the OR gate 179 in view of this discussion. If the TV camera sees the white streak in the middle of the bottle, and therefore the BN signal on line 178 is no longer present, then the AND gate 171 would stop transmitting B pulses and the true B value would be lost. However, because of the inputs to the AND gate 159, after the twelfth line and after the BN signal has been initially generated, there will be a signal through the OR gate 179 so that in the event the signal on line 178 fails, the B signals will still be counted and the true value of the B measurement will be tabulated in the counter 175.

Now consider what the output from the AND gate 159 accomplishes after it passes the inverter 157. Prior to the system reaching the twelfth line, the output signal from the inverter 157 was a high signal which enabled the BNLP signal to reset the flip-flop 145 when the video began, thus terminating the ACP pulses to the counter 153 and the BNTP signal reset the flip-flop 163 to stop the AB pulses at the end of the video. If the system were to see the white lens effect, as mentioned earlier, we would be apt to get spurious BNLP signals and BNTP signals, and the system must avoid this. Accordingly after the twelfth line, when the TV camera sees the edge of the bottle, the BNLP signal is generated and transmitted to the AND gate 155. At that point in time, the flip-flop 209 has been reset from the previous compare, and is simply being set by that same BNLP signal. The inherent delay in setting the flip-flop 209, having the signal pass through the AND gate 159 and through the inverter 157, will permit the BNLP signal on line 211 to pass the AND gate 155 and reset the flip-flop 145 so that the ACP pulses will be terminated. However, almost instantaneously after the flip-flop 145 has been reset, the signal from the flip-flop 209 passing through the AND gate 159 will provide a high signal to the inverter 157, and hence a low signal therefrom will block the AND gate 155 so that any spurious BNLP signals will not be transmitted through the AND gate 155.

In a similar fashion if any spurious BNTP signals should be generated, because of the white lens effect, they would reset the flip-flop 163 early; i.e., because the AN signals were transmitted to the counter 169, and therefore the output signal from the inverter 157, after the twelfth line has been reached, blocks the AND gate 161 until "23" pulses before the end of the scan. At "23" pulses before the end of the scan, the flip-flop 209 is reset and hence the output from the AND gate 159 is low, providing a high output from the inverter 157, so that the BNTP signal can be transmitted through the AND gate 161 to reset the flip-flop 163 and terminate the $\overline{AB}$ signals as is proper.

Figure 4:
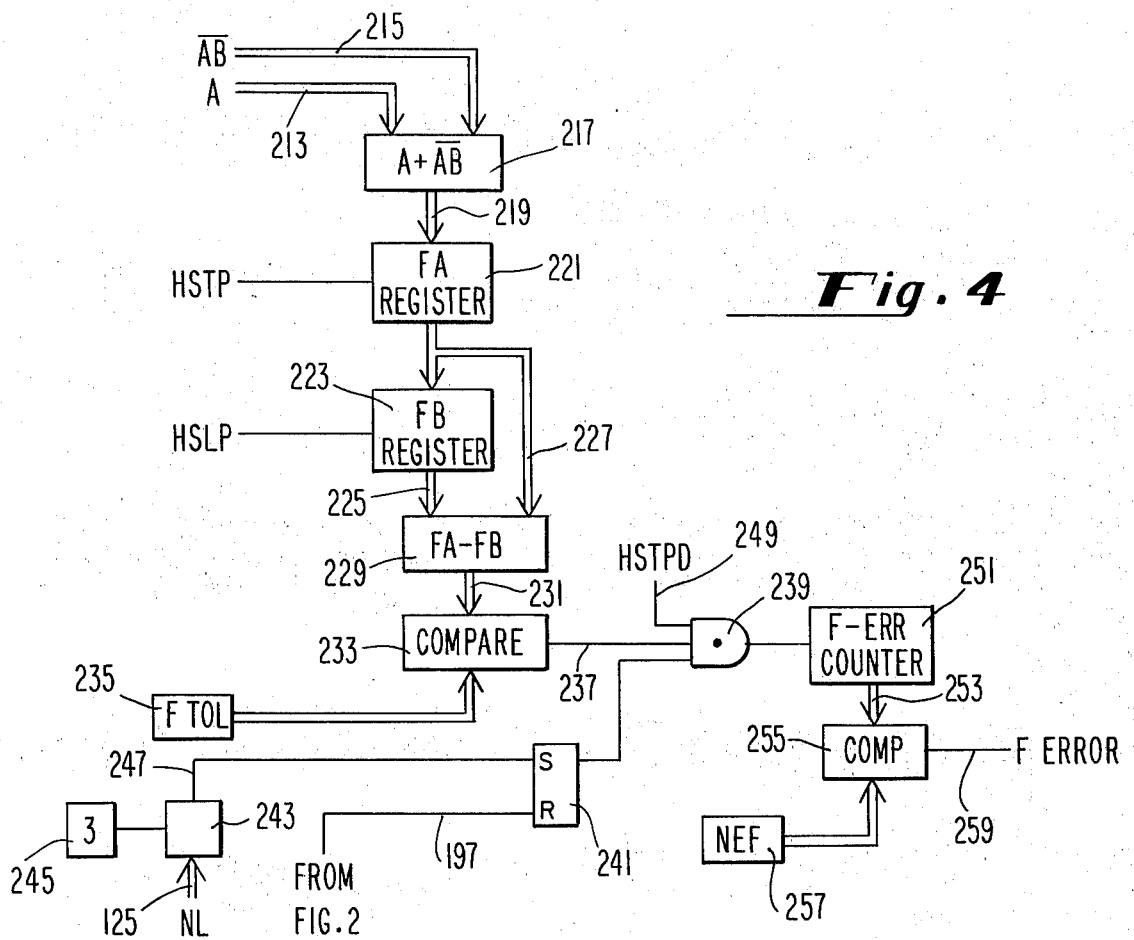
FIG. 4 is a logic diagram showing the circuitry to produce an error signal related to a symmetry test.

Consider now FIG. 4 which shows the logic circuitry for determining whether or not A + $\overline{AB}$ is constant in order for the system to decide whether or not the bottle has proper symmetry, as discussed earlier. In FIG. 4, the A signals are shown coming in on channel 213 from FIG. 2, and the $\overline{AB}$ signals are shown coming in on channel 215 from FIG. 2. The A signals and the $\overline{AB}$ signals are added together in the summmation circuitry 217. The summation circuitry 217 can be any typical adding circuitry such as the 7483 manufactured by Signetics, Inc.

The information coming into the adder circuitry 217 will be continually added and the output will be transmitted on the channel 219 to the register 221. However, the register 221 will not accept that information, or will not temporarily store that information, until the HSTP signal of the next scan. Accordingly, when the next scan starts, the HSTP signal will condition the register 221 to accept the information from the adder circuit 217. On the following scan, the new information will be accumulated in the adder circuit 217 and this information will be transmitted to the register 221 but will not be received thereat. In the third scan, the HLSP signal will gate the information from the register 221 into the register 223 while immediately therafter the HSTP signal will gate the information from the adder circuit 217 to the register 221. Accordingly, there will be A + $\overline{AB}$ signal information from a first scan in register 223 and from a second scan in register 221. The signal information from the registers 223 and 221 are respectively transmitted on the channels 225 and 227 to the subtract circuitry 229. The subtraction circuitry 229 can be any well-known subtraction circuitry, such as Model No. 7483 manufactured by Signetics, Inc. The subtraction circuitry 229 will subtract the first A + $\overline{AB}$ information from the second A + $\overline{AB}$ information and transmit the difference on channel 231 to the compare circuit 223. The other input to the compare circuit 233 is from the tolerance switches 235. The tolerance switches 235 provide a value which represents a permissible amount of discrepancy and if the value on channel 231 does not exceed the value set in the tolerance switches 235, then there will be no error signal transmitted on line 237. However, if the value on 231 exceeds the tolerance, then there will be an error signal generated on line 237, which will be transmitted to the AND gate 239.

The other two inputs to the AND gate 239 are the HSTP delayed signal (HSTPD) as well as the output from the set side of the flip-flop 241.

It will be recalled that the symmetry check is to determine the flatness at the top of the bottle, and the system is predicated on the belief that this can be checked between the third line of scanning and the twelfth line of scanning. Accordingly, checking for $A + \overline{AB}$ equal to a constant is checked between the third line and the twelfth line. The flip-flop 241 has an input from the compare circuit 243. The compre circuit 243 has the number "3" switch input from the switch circuit 245 as well as the NL input from channel 125 (FIG. 2). When NL reaches the value 3, the output from the compare circuit 243 will be transmitted on line 247 to set the flip-flop 241, thereby providing a second input to the AND gate 239. During that same scan, the HSTPD signal will be transmitted on line 249 to condition the AND gate 239 to provide an error signal to the error counter 251 if, in fact, an error has been determined. When the NL count gets to twelve, there will be an output signal on line 197 (FIG. 2) transmitted to reset the flip-flop 241, thereby terminating any possibility of sending error signals to the error counter 251. Now the only reason that the output of the AND gate 239 is sent to an error counter rather than to simply generate an error signal is that the user of this system may want to tolerate a certain number of errors; and if this be the case, the error counter output is transmitted on channel 253 to the comparator 255. The comparator 255 is similar to the comparators used throughout the system. Also transmitted to the comparator 255 is the output from the error switches 257. Whatever the tolerable number of errors might be, it is set in the switches 257 to be sent to the comparator 255. If the count in the error counter 255 exceeds the value of 257, then there is an error signal transmitted on the line 259, which error signal can be used to do many things. The error signal can alert the user that there has been an error or it can automatically shutdown the production.

Figure 5:
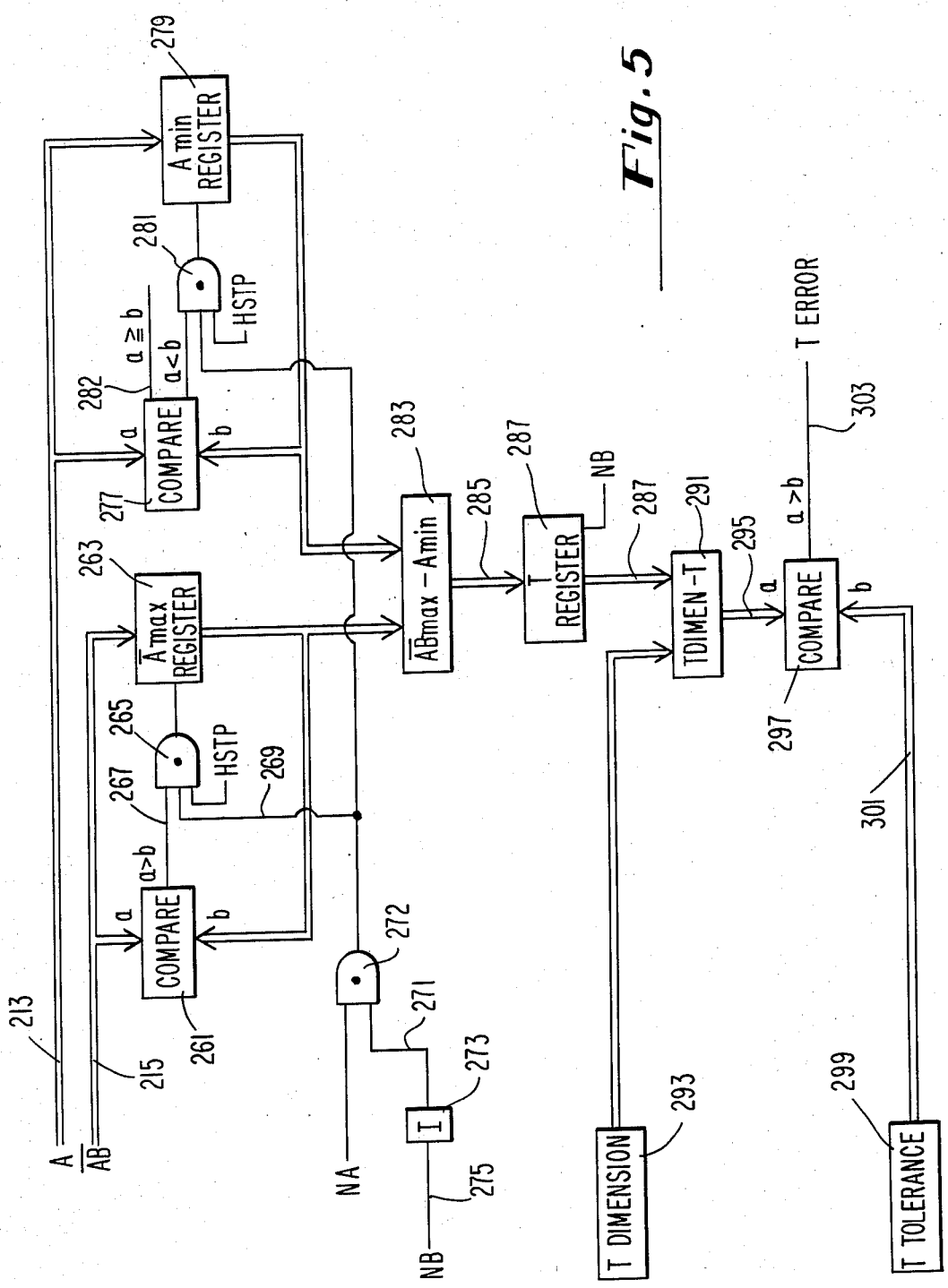
FIG. 5 shows the logic circuitry necessary to produce an error signal related to a thread dimension measurement.

Consider now FIG. 5 which is the logic circuitry necessary to generate an error related to the measurement of the thread. We find in FIG. 5 that the A value signals are transmitted on channel 213 from FIG. 2 and that the $\overline{AB}$ value signals are transmitted on channel 215 from FIG. 2. The $\overline{AB}$ value signals on line 215 are transmitted to a compare device 261 as well as to an $\overline{AB}$ max register 263. If we examine FIG. 1 we can see that if we determine when the $\overline{AB}$ value goes through a maximum value we have $\overline{AB}$ max, then we have determined the right-hand most value of the thread, and similarly if we can determine when the A value goes through its lowest value, we have determined the left-hand most value of the thread. The circuitry in FIG. 5 accomplishes the determination of these peak points.

The signals on the channel 215 are transmitted to the compare circuit 261 and the $\overline{AB}$ max register 263 simultaneously. However, the signals will not be accepted by the $\overline{AB}$ max register 263 unless the AND gate 265 is transmitting a signal thereto.

It can be noted that the inputs to the AND gate 25 are the signal on line 265 which indicates that "$a$" must be greater than "$b$", and the signal on line 269 which indicates that the value NA has been determined but the value NB has not been determined. If we consider FIG. 1, we see that this would be in the time frame, scan-wise, between NA and NB where the threads are located. The signal NA is the signal from the flip-flop 192, and, of course, the signal on line 271 which is "not NB" is from the inverter 273, whose input is NB on line 275 from the flip-flop 131.

Accordingly, then, between the positions NA and NB, as seen in FIG. 1, we find the line 269 is high to further condition the AND gate 265. The third input to the AND gate 265 is the HSTP signal.

During a first scan, the value of $\overline{AB}$ will be transmitted to the compare unit and to the $\overline{AB}$ max register 263. Assume for the moment that there is no value in the $\overline{AB}$ max register, then indeed the compare unit 261 would be providing an "$a$" greater than "$b$" signal on line 267 and the AND gate 265 would be fully conditioned at HSTP time, to permit the AB max register to accept the signals on channel 215. At the next scan time, let us assume that the value $\overline{AB}$ increases and that value is transmitted to the compare unit 261 at HSLP time of that scan. A comparison is made with the value in the $\overline{AB}$ max register from the previous scan, and at HSTP time the AND gate 261 is fully conditioned so that the $\overline{AB}$ max register accepts the information from the second scan. If we consider that the value $\overline{AB}$ increases the foregoing operation will continue until the value $\overline{AB}$ peaks and starts to decrease, at which time there will be no output from the compare unit 261. Hence the last value in the $\overline{AB}$ max register will represent $\overline{AB}$ max as shown in FIG. 1.

The determination of A min is virtually identical to that just described in connection with the determination of $\overline{AB}$ max. The signals on channel 213 are sent to the compare unit 277 and to the A min register 279. As long as the "$a$" value is less than the "$b$" value; i.e., the value in the A min register, new values will be inserted into the A min register. When finally the value "$a$" is greater than the value "$b$" from the A min register, there will no longer be any signal from the AND gate 281 and hence the last value registered in the register 279 will be the true A min value.

The $\overline{AB}$ max value as well as the A min value are transmitted to the subtraction circuit 283 whereat they are substracted and the quotient therefrom is transmitted on channel 285 to the T register 287. The value on 285 is gated into the T register at NB time which is the time at which the thread determinatin is considered to have been made.

The value of the T register is transmitted on the channel 289 to the subtract circuit 291. The other input to the subtract circuit 291 is from the T dimension memory portion 293 whereat the standard value of the T dimension has been stored.

In the subtraction circuit 291, the standard value from memory 293 will have subtracted therefrom the value of T measured by subtracting A min from $\overline{AB}$ max as just described. If there is a difference between the T dimension of the standard bottle and the T value derived from the subtraction of A min from $\overline{AB}$ max, there will be produced an error signal on channel 295. The output from the subtract circuit 291 is an 8 bit binary output which can carry 8 signals representing a digital value.

As with the other error circuits, the system permits the user to tolerate a certain amount of error. If that be the case with the user, then the tolerance is inserted in the switches of the tolerance insert device 299, and that value is transmitted to the compare circuit 297 by virtue of the channel 301. If the difference on 295 is greater than the tolerance on 301, then there is an output on line 303 indicating that the measurement of the thread is in greater error than the tolerance would permit.

Figure 6:
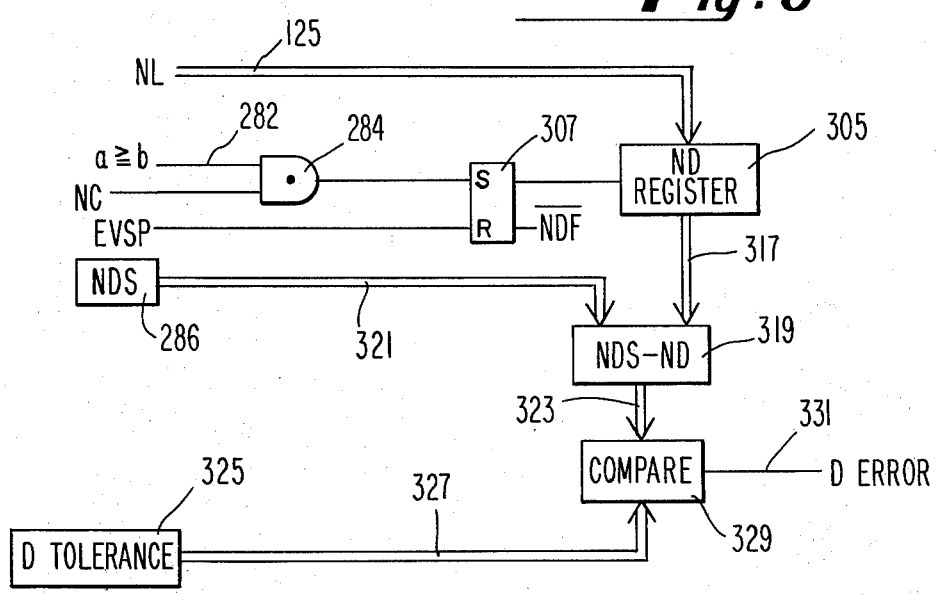
FIG. 6 shows the logic necessary to produce an error signal related to determining the point at which the binder ring is located.

Now consider the logic circuitry shown in FIG. 6, which is the circuitry necessary to generate an error of the D dimension. It will be recalled that the fabricator of the bottle wants to know when the D dimension has been determined because that is the point at which the binding ring of the twist-off cap is crimped.

In FIG. 6 it will be noted that the number of lines which have been counted in accordance with the circuitry discussed in FIG. 2 is transmitted on line 125 from FIG. 2 to the ND register 305. The ND register 305 is used to record the number of lines which have been scanned before the point ND is reached, and this, of course, determines the D dimension, or the point on the bottle where the binding ring will be crimped.

It will be recalled that in accordance with the discussion of FIG. 1, we were seeking to establish the first time that A min was determined after the point NC had been reached, and the determination of this second A min would give us the dimension D. The value of A min in register 279 will not be disturbed after NB has been generated because gate 281 will not be fully conditioned. However the value of A is still transmitted to the compare unit 277. We want to find $a \geq b$ or the value of A greater than or equal to A min after NC time. Hence the signal on line 282 is transmitted to gate 284 in FIG. 6. AND gate 284 is further conditioned by the NC signal. Accordingly after the NC signal has been generated, the only time that $a \geq b$ will be at D time. This can be gleaned from examining FIG. 1, section 280. When $a \geq b$, the signal on line 282 passes gate 284 to set flip-flop 307 and stop register 305 from receiving any additional NL signals. Accordingly, the value in the ND register should be the value of the dimension D. The compare unit 277 can be Model No. 7485 manufactured by Signetcis, Inc.

The value of D from the ND register 305 is transmitted on the channel 317 to the subtract circuit 319. Also transmitted to the subtract circuit 319 are the signals representing the standard value NDS along channel 321. The values representing the standard NDS are from the memory unit and these signals represent the D dimension of the standard bottle. The NDS device 286 can be a set of switches or a decade counter, or a core memory-some means for storing the standard value.

Accordingly in the subtract circuit 319, the D measurement of the bottle in production is subtacted from the D measurement of the standard; and if there is a difference, it is transmitted on channel 323. As with the other error circuits, the system permits the user to tolerate some discrepancy and the D dimension tolerance is set up in the switches represented by the D tolerance switches 325. The value of the tolerance is transmitted on channel 327 to the compare unit 329. If the error is larger than the tolerance then the error signal will be produced on line 331. On the other hand, if the error on line 323 does not exceed the tolerance on line 327, there will be no error on line 331.

The system accomplishes one other major function. It does a line-by-line check. If we look at FIG. 1, the line-by-line check is accomplished between NL = 1 and NL = NA, and then starts over again on a line-by-line check between NL = NB and NL = ND. What is meant by a line-by-line check is that the B value; i.e., the actual distance across the bottle, is compared on every scan with the standard bottle. If there are a sufficient number of distortions, the bottlw will be rejected.

Figure 7:
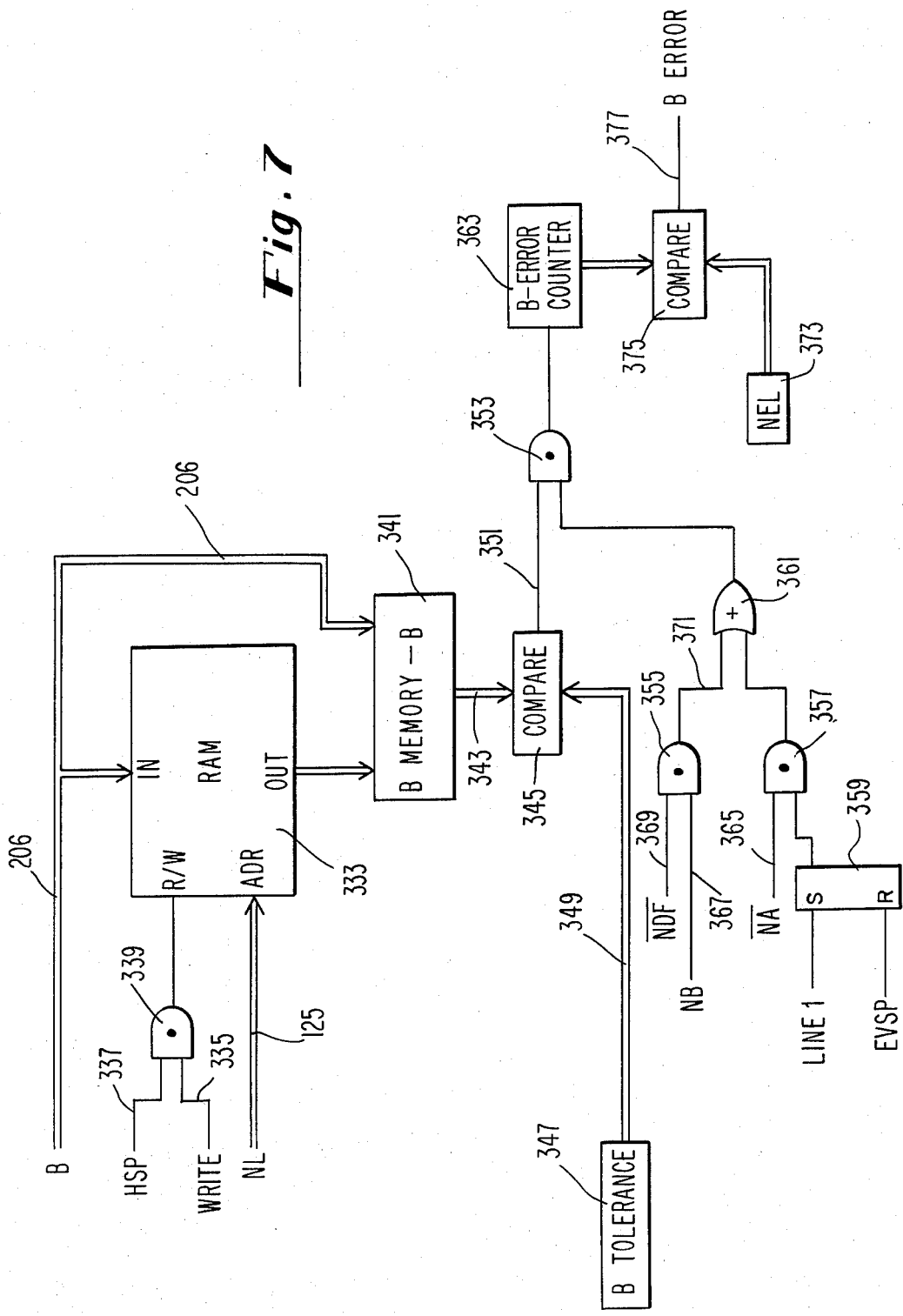
FIG. 7 shows the logic necessary to produce an error signal related to measuring the contour of the bottle.

If we examine FIG. 7, we find the logic for accomplishing the line-by-line check. In FIG. 7, it will be noted that there is a random access memory 333 which has an NL input transmitted to the addressing circuitry thereof. Now the random access memory 333 can be any standard random access memory which has a means for addressing the memory and also a means to cause the memory to either have information written thereinto or read therefrom. Such a standard random access memory in the preferred embodiment is a Model 93410 manufactured by Fairchild, but indeed other random access memories can be used. The random access memory 333 operates such that upon the occasion that a plurality of signsls, representing an address, are transmitted on channel 125 from FIG. 2, the location in the memory that is addressed will read the information therefrom. It is only on the occasion that the write signal on line 335 is present along with the horizontal sync pulse signal on line 337 that the AND gate 339 will condition the memory locations to write the information being transmitted on channel 125. Bearing that operation of the memory in mind, we find that when the standard bottle is in the scanning location, the B signals on channel 206 from FIG. 2 are transmitted to the random access memory 333 as well as to the subtract circuitry 341. The information transmitted to the random access memory 333 will be written into the locations designated by the information on NL. The NL value, of course, represents the number of lines that are being counted so that the first line that is counted will provide a digital signal 1, and therefore the B value will be written into the first location in memory. The second B value will be written in the second location in memory, etc. Assuming that the B information for each of the line designations between NL=1 and NL = NA as well as the B information for each of the locations between the NL = NB and the NL = ND have been written into the memory for the standard, then let us consider how the system operates to effect a comparison between this B information so that a line-by-line check of the profile of the production bottle can be accomplished. Once the standard information has been written into the random access memory 333 and a scan of a production bottle commences, it will be recalled that the first NL signal which is NL = 1 will only be transmitted after an Enable Signal has been generated. Hence the first information on the NL channel 125 is the number one when NL = 1, and the value of B of the first line is transmitted from the random access memory to the subtract circuitry 341. At the same time, the signals on channel 206 are transmitted to the subtract circuitry 341 representing the value of B of the production bottle at line 1, and there is a subtraction effected in between these two values. The difference between the B value at NL = 1 of the production bottle is transmitted on channel 343 to the compare unit 345. The system enables the user to tolerate some discrepancies in that difference and the B tolerance switches 347 are set to provide the tolerable discrepancy. The value of the tolerable discrepancy is transmitted on channel 349 to the compare circuit 345. If the difference between the B value of the standard at NL = 1 and the B value of the production bottle at NL = 1 is sufficiently greater than the tolerance on line 349, then there will be an error signal transmitted on line 351 to the AND gate 353.

For each line between NL-1 and NA, a similar comparison will be made between the B values, and each time there is an error that exceeds the tolerances there will be a signal on line 351. Now the system operates such that it will tolerate a certain number of errors that exceed the tolerance value. The system only wants to look at the comparison on the line-by-line basis between NL-1 an NL = 1 and NL = NA as well as between M = NB and NL = ND. Therefore the information between NL = NA and NL = NB is not to be considered in this line-by-line comparison. The exclusion of the information between NL = NA and NL = NB is accomplished by the logic circuitry including the AND gates 355 and 357. The circuitry on FIG. 7 provides that as far as a total comparison of the number of errors related to the B dimension is concerned, the system will statt the examination with line 1. The flip-flop 359 is reset with an EVSP signal and at line 1 the flip-flop 359 is set or turned on. When the flip-flop 359 is set, it provides one input to the AND gate 357 to partially condition that AND gate. AS long as NL = NA has not been reached, then the "not NA" signal will be high providing the other input to the AND gate 357, and hence a high output from the AND gate 357 will be transmitted to the OR gate 361. The output from the OR gate 361 is transmitted to the AND gate 353, and hence any errors occurring after line 1 and before NA is generated will be transmitted through the AND gate 353 to the B error counter 363. The B error counter 363 counts the number of discrepancies between the B value of the standard bottle and the B value of the production bottle, which errors exceed the tolerance set up in the switches 347. When NL gets to the value NA, then the line 365 will no longer be high and hence the AND gate 357 will no longer provide an output through the OR gate 361 to condition the AND gate 353. Hence any errors in B values which may occur between NL = NA and NL = NB will not be passed to the B error counter 363. When the value NB has been determined, as we discussed in our study of FIG. 2, there will be a high signal on line 367 to partially condition the AND gate 355. As long as the ND signal has not yet been generated as shown in FIG. 6, then the "not ND" signal will appear as a high signal on line 369. Accordingly when NB has been generated to provide a high signal on 367, the AND gate 355 will be fully-conditioned to provide an output on line 371 which will pass through the OR gate 361 to fully condition the AND gate 353, and once again provide error signals to the error counter 363 if in fact the B value of the production bottle differs sufficiently from the B value of the standard bottle. The system operates to permit the user to tolerate a certain number of B errors. The number of B errors that will be tolerable is set in the error switch device 373 and a comparison is made between the number accumulated in the error counter 363 and the tolerable number of errors set in switches 373. If the number of actual errors accumulated exceeds the number of tolerable errors, then the compare circuitry 375 will produce an output on line 377 indicating that the contour of the production bottle on a line-by-line check is sufficiently different from the standard, that the production bottle should be rejected.

We claim:

1. A system for monitoring three dimensions of an item which is being fabricated and which has an irregular shape including a plurality of critical width dimensions and critical length dimensions and requiring a particular depth characteristic and which item is initially difficult to physically inspect comprising in combination: means to effect an image of said item which image can be seen and recorded by a TV camera means; TV camera means disposed to see and temporarily record each of said item images whereby each of said item images can be scanned to translate said recorded images into electronic signals related thereto; first electronic circuitry means connected to said TV camera means to receive said electronic signals and in response thereto to generate first signals representing different width dimensions of said item image; second electronic circuitry means connected to said TV camera means to receive said electronic signals and in response thereto to generate second signals representing different lengths of said item image; third electronic circuitry means connected to receive said first and second signals and to perform arithmetic operations thereon to generate third signals representing said particular depth characteristic and to generate fourth signals representing critical width dimensions of said item and to generate fifth signals representing critical length dimensions of said item; fourth electronic circuitry means into which electronic signals can be stored to represent a standard item image, said fourth electronic circuitry means being formed to provide sixth signals representing critical width dimensions and critical length dimensions of said standard item image; fifth electronic circuitry means connected to said third and fourth electronic circuitry to monitor said particular depth characteristic signal for detection of an error thereof and to compare said fourth and fifth signals with said sixth signals to detect an error therebetween, whereby said item is either rejected or accepted as an approved item.

2. A system according to claim 1 wherein said item is a bottle shaped to have a binding ring crimped therearound at a certain location and wherein said third electronic circuitry means includes logic circuitry to determine the critical length on said image where said binding ring would be crimped and where said fifth circuitry means compares that location value with a counterpart location on value of a standard bottle image.

3. A system according to claim 1 wherein said item is a bottle which acts as a lens to certain light directed thereto and provides a light streak in accordance therewith and whereby said third electronic circuitry means includes logic circuitry to ignore signals being generated by that portion of said item image whereat said light streak is located.

4. A system accoding to claim 1 wherein said item is carried on a conveyor belt and wherein said first electronic circuitry means includes logic circuitry to compensate in generating said first signals for the movement of said conveyor belt.

5. A system according to claim 1 wherein the first scan of said item image is considered as unreliable and wherein said first electronic circuitry means includes logic circuitry which ignores said first scan information and commences using information from a second scan of said item image.

6. A system according to claim 1 wherein said fifth circuitry means includes logic circuits which compare said item image with said standard item image on a scanned line by scanned line basis for a particular length.

7. A system according to claim 1 wherein said TV camera means includes a plurality of TV cameras and said first, second, third fourth and fifth circuitry means is each connected alternatively to each of said TV cameras.

8. A system according to claim 1 wherein said TV camera means is disposed to view said item from a position above said item.

9. A system according to claim 1 wherein said fifth electronic circuitry means processes said third signals to determine therefrom whether or not said item image is symmetrically shaped.

10. A system according to claim 1 wherein said item is a bottle having a threaded top and wherein said third circuitry means includes logic circuits which subtract one width dimension from a second width dimension to determine whether or not the threads of said threaded top are within acceptable tolerances with respect to the dimensions of a standard bottle.

* * * * *